US006731787B1

(12) United States Patent
Vacca et al.

(10) Patent No.: US 6,731,787 B1
(45) Date of Patent: *May 4, 2004

(54) SYSTEM AND METHOD FOR DETERMINING RETICLE DEFECT PRINTABILITY

(75) Inventors: Anthony Vacca, Cedar Park, TX (US); Thomas Vavul, San Francisco, CA (US); Donald J. Parker, San Jose, CA (US); Zain Saidin, Sunnyvale, CA (US); Sterling G. Watson, Palo Alto, CA (US); James N. Wiley, Menlo Park, CA (US)

(73) Assignee: KLA-Tencor Corporation, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/137,133

(22) Filed: Apr. 30, 2002

Related U.S. Application Data

(60) Continuation of application No. 09/559,512, filed on Apr. 27, 2000, now Pat. No. 6,381,358, which is a division of application No. 08/933,971, filed on Sep. 19, 1997, now Pat. No. 6,076,465.
(60) Provisional application No. 60/026,426, filed on Sep. 20, 1996.

(51) Int. Cl.[7] .................................. G06K 9/00
(52) U.S. Cl. ................ 382/145; 382/144; 348/86
(58) Field of Search ................ 382/141–151; 348/86, 87, 125, 126; 356/394

(56) References Cited

U.S. PATENT DOCUMENTS

| 4,123,170 A | 10/1978 | Uchiyama et al. |
| 4,247,203 A | 1/1981 | Levy et al. |
| 4,579,455 A | 4/1986 | Levy et al. |
| 4,805,123 A * | 2/1989 | Specht et al. ............... 382/144 |
| 5,018,212 A | 5/1991 | Manns et al. |
| 5,586,058 A | 12/1996 | Aloni et al. |
| 5,619,429 A | 4/1997 | Aloni et al. |
| 5,781,657 A | 7/1998 | Masuda |
| 6,076,465 A | 6/2000 | Vacca et al. |
| 6,381,358 B1 * | 4/2002 | Vacca et al. ............... 382/145 |

* cited by examiner

Primary Examiner—Vikkram Bali
(74) Attorney, Agent, or Firm—Beyer Weaver & Thomas, LLP

(57) ABSTRACT

A method and software program for determining printability of a defect on a reticle or photomask onto a substrate during processing. That is performed by creating a pixel grid image having a plurality of individual pixel images showing the defect. A gray scale value is assigned to each pixel image of the pixel grid image and a probable center pixel of the defect is selected. Then the polarity of the defect is determined, with a coarse center pixel of the defect optionally selected using the probable center defect and polarity of the defect. If a coarse center pixel is selected, then a fine center of the defect can optionally be selected from the coarse center pixel and polarity of the defect. From the center pixel the physical extent of the defect can be determined followed by the determination the transmissivity energy level of the physical extent of the defect. Optionally, the proximity of the defect to a pattern edge on the reticle or photomask can be determined using the physical extent and polarity of the defect. Then the printability of the defect can be determined from the transmissivity energy level of the defect and characteristics of the wafer fabrication process being used to produce the substrate from the reticle or photomask.

8 Claims, 4 Drawing Sheets

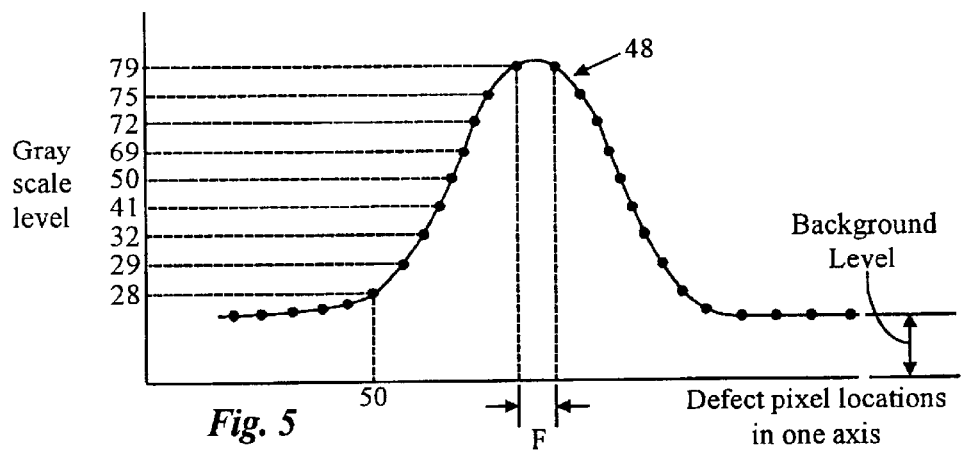
Fig. 5
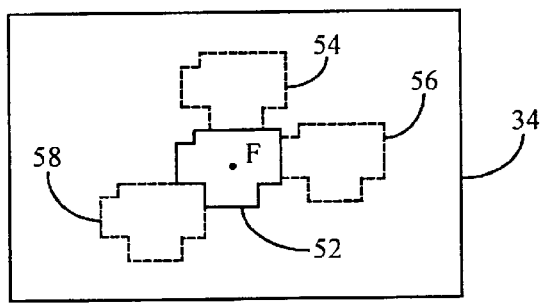
Fig. 6
Fig. 7b
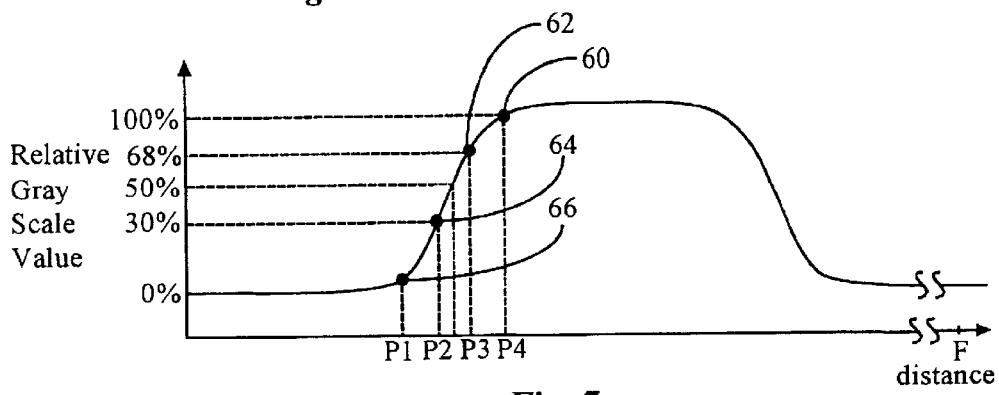
Fig. 7a

SYSTEM AND METHOD FOR DETERMINING RETICLE DEFECT PRINTABILITY

CROSS-REFERENCE TO RELATED APPLICATIONS

This application is a continuation of U.S. application Ser. No. 09/559,512, now U.S. Pat. No. 6,381,358, filed Apr. 27, 2000, entitled "System and Method for Determining Reticle Defect Printability," which is a divisional application of application Ser. No. 08/933,971, now U.S. Pat. Ser. No. 6,076,465, filed on Sep. 19, 1997, which claimed priority from a Provisional application having Serial No. 60/026,426, filed on Sep. 20, 1996.

This patent is related to U.S. Provisional Patent Application No. 60/375,091, entitled "Closed Region Defect Detection System," filed on Apr. 23, 2002, and to U.S. patent application Ser. No. 10/325,023, entitled "SURFACE INSPECTION SYSTEM AND METHOD USING SUMMED LIGHT ANALYSIS INSPECTION SURFACE," filed on Dec. 19, 2002.

FIELD OF THE INVENTION

The present invention relates generally to electro-optical inspection systems, and more particularly to an automated reticle inspection system and method for determining which defects in a reticle will print on the substrate and effect the performance of a completed semiconductor device.

BACKGROUND OF THE INVENTION

Present reticle and photomask inspection systems currently identify defects on reticles and photomasks merely as defective pixels. No effort is made to determine printability and the ultimate impact of identified defects on a finalized semiconductor device. That approach has been satisfactory in the past given the trace widths and number of components to be implemented on a single substrate and in a single chip.

However new technology has continued to push the line and component density on a single semiconductor substrate, and in a single chip, to greater and greater levels with ever narrower line widths being required. That being true, and given the previous criteria as to what defects are a potential problem, smaller and smaller anomalies in reticles and photomasks are being considered a defect. Given the current technology, anomalies of well below one micron in size (down to 200 nanometers in some cases) are being considered defects. Therefore, inspection machines have been refined to detect these ever smaller anomalies on reticles and photomasks.

Currently, in the semiconductor industry, complex reticles and photomasks that can cost tens of thousands of dollars to produce are being scraped since it is believed that even the smallest defect in one reticle or photomask used in the production of a substrate may have a detrimental effect on the performance of the final semiconductor component.

What is needed is a method and system that not only identifies the ever smaller anomalies on a reticle or photomask as a defect; but which goes further and considers other characteristics, the location of the defect, and the line patterns on the reticle or photomask, to determine whether or not each individually identified defective pixel will print onto the semiconductor substrate. If this is accomplished, many reticles and photomasks that are currently being scraped could instead be used with no detrimental effect on the operation of the final semiconductor component, thus reducing the cost of production of semiconductor devices. It is believed that the present invention provides that capacity.

BRIEF SUMMARY OF THE INVENTION

The present invention includes a method and software program for determining printability of a defect on a reticle or photomask onto a substrate during processing. That is performed by creating a pixel grid image having a plurality of individual pixel images showing the defect. A gray scale value is assigned to each pixel image of the pixel grid image and a probable center pixel of the defect is selected. Then the polarity of the defect is determined, with a coarse center pixel of the defect optionally selected using the probable center defect and polarity of the defect. If a coarse center pixel is selected, then a fine center of the defect can optionally be selected from the coarse center pixel and polarity of the defect From the center pixel the physical extent of the defect can be determined followed by the determination the transmissivity energy level of the physical extent of the defect. Optionally, the proximity of the defect to a pattern edge on the reticle or photomask can be determined using the physical extent and polarity of the defect. Then the printability of the defect can be determined from the transmissivity energy level of the defect and characteristics of the wafer fabrication process being used to produce the substrate from the reticle or photomask.

BRIEF DESCRIPTION OF THE DRAWINGS

The invention, together with further advantages thereof, may best be understood by reference to the following description taken in conjunction with the accompanying drawings in which:

FIG. 5 is a representative gray scale value variation for a pixel of a defect along one axis with reference to the spacing between the center pixel of the defect to those pixels extending away from the center pixel.

FIG. 6 illustrates the determined extent of a defect in the pixel grid image and adjacent groupings of pixels in the same size and shape as the extent of the defect.

FIG. 7a illustrates a typical gray scale value variation for the pixels adjacent to each side of, and those that make up the edge of, a line on a reticle.

FIG. 7b illustrates the use of linear sub-pixel interpolation to locate the edge of a line on a reticle.

DETAILED DESCRIPTION OF THE INVENTION

There are numerous inspection machines available that have the capability of identifying defects on a reticle or photomask. An example of such a machine that performs the inspection automatically by either die-to-die or die-todatabase inspection is described in detail in European Patent Specification EP 0532927B1 published Feb. 21, 1996, entitled "Automated photomask inspection apparatus", and which is incorporated herein by reference. In performing that inspection, the above identified inspection machine, and other similar machines, scans the reticle or photomask and pixelizes the image, saving the pixel location information for each of the scanned regions where there is not agreement between the dies (in die-to-die) or between the die and the data base (in die-to-data base). A typical pixel size used by such inspection machines is a 0.25 .mu.m square. What is not determined by the currently available defect detection machines is the transmittable energy level of light through the groups of pixels that constitute each defect; more specifically the transmittable energy level of the radiation frequency used by the steeper to expose a semiconductor wafer to the pattern on the reticle or photomask prior to each chemical processing step of the wafer in the production of the finished semiconductor component.

It has been discovered that there are numerous factors that contribute to whether or not a defect on a reticle or photomask will print on a substrate. The size of such a defect is only one of those factors. It has also been determined that the energy level that will pass through such a defect is equally important to being able to make a determination as to whether or not such a defect will print onto a substrate that is exposed to such a reticle or photomask. There are still other factors that contribute to whether or not such a defect will print onto a substrate.

The primary factor as to the printing of a defect in a reticle on a substrate is the transmittable energy level through that defect. It is clear that if the defect in question is a type that is not transmissive, there can be no trace of that defect on the substrate exposed by the reticle in which the defect is contained, regardless of the size of that defect.

There are numerous other factors that influence whether or not a defect prints onto a substrate. Those include, among other factors, the type of resist used on the substrate, line width size, stepper type, numerical aperture of the stepper, focus of the stepper, radiation frequency of the stepper, exposure time of the stepper, etc.

Figure 1:
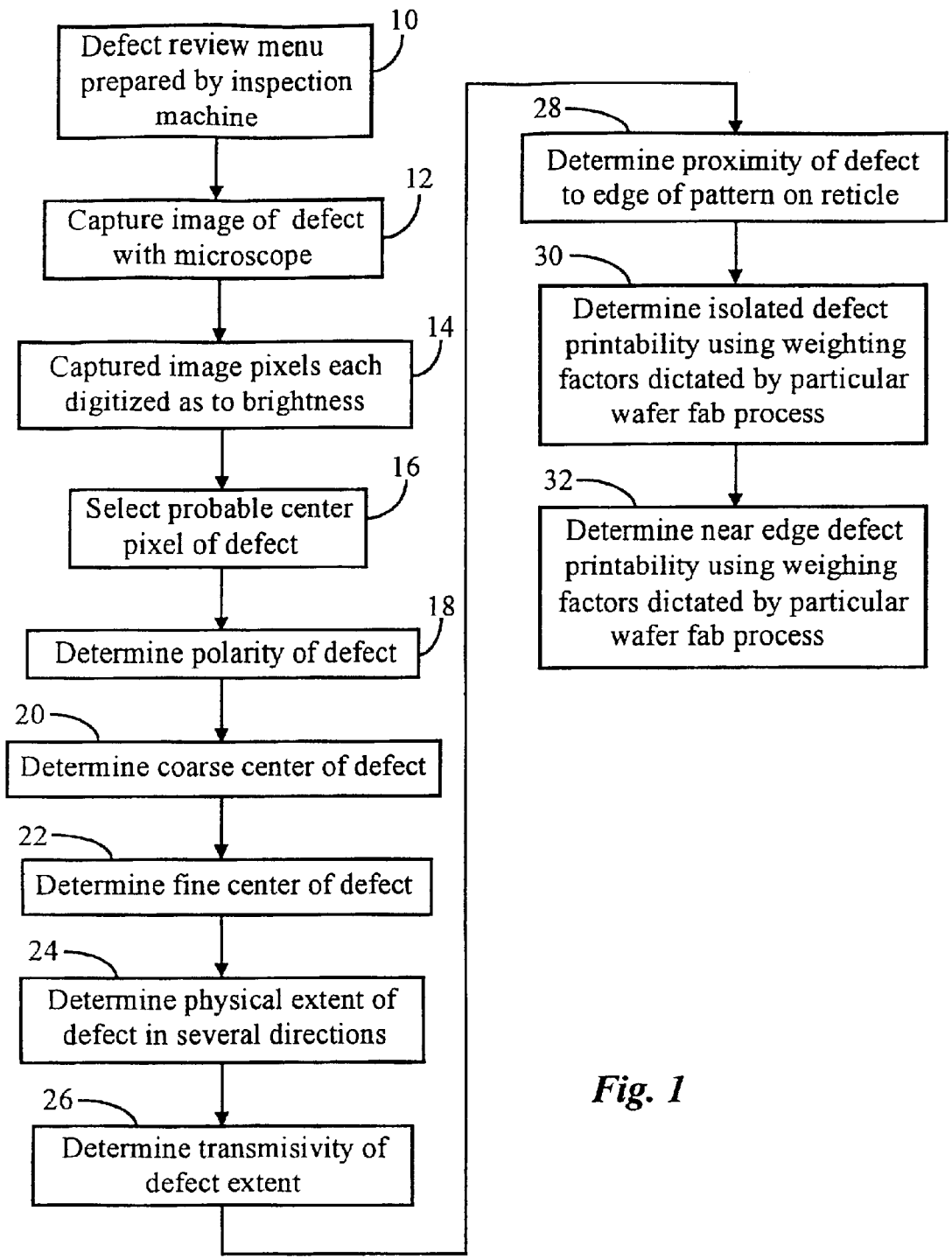
FIG. 1 is a general flow diagram that illustrates the steps of the present invention.
Figure 8:
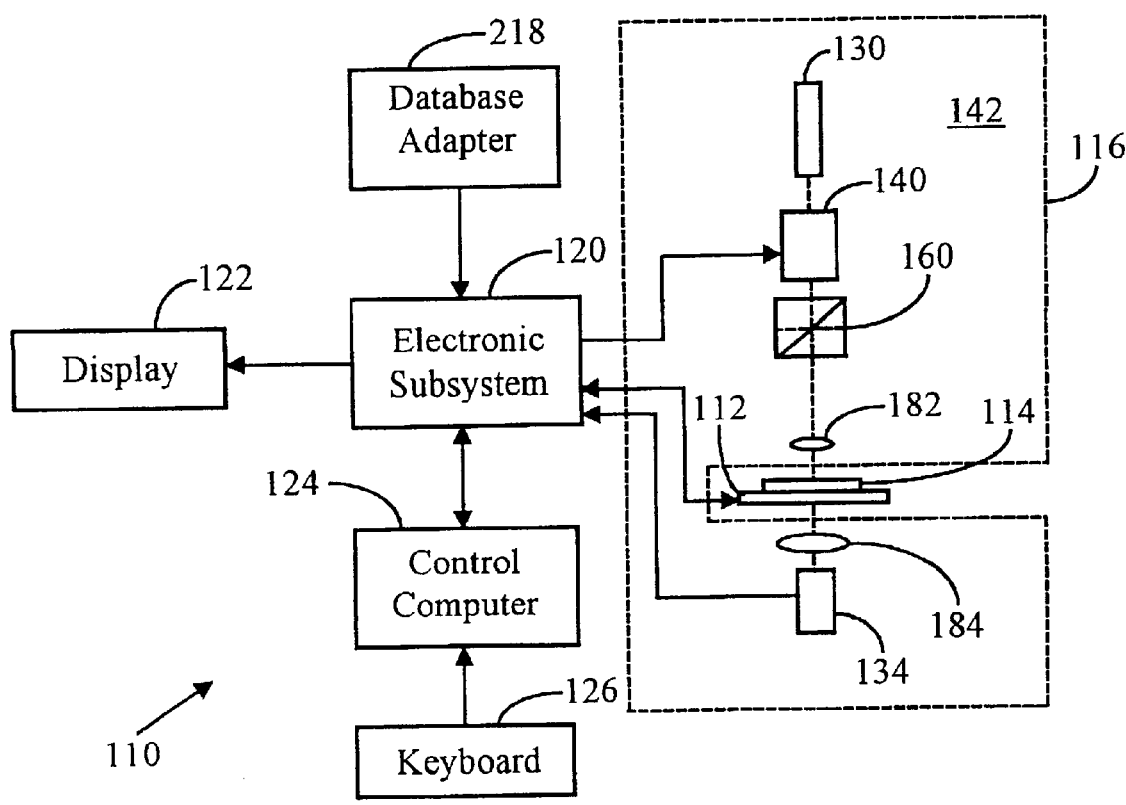
FIG. 8 is a simplified functional block diagram of a prior art mask inspection system.

Referring to FIG. 1, the actual process of the present invention thus begins with the defect review menu (10) that the prior art inspection machine creates. A microscope is then used, by an operator or automatically, to capture the image of a defect (12) from the defect review menu by scanning that defect image and creating a pixel grid image (e.g., 256 by 256 pixels with the pixel size being 0.25 .mu.m) of a defective area. Then, using a gray scale resolution of 256 levels, each pixel in that captured image is digitized (14) by assigning a gray scale value that corresponds to the brightness or darkness of that pixel from 0 to 256, with 0 being for opaque pixels and 256 being for fully transmissive pixels of the defective area of the photomask. FIG. 8 is a prior art mask inspection system (FIG. 1 of European Patent Specification EP 0532927B1) that could be used to perform this function with optical subsystem 116 acting as the microscope, and delivering the image from the reticle 114 to electronic subsystem 120, all under the control of control computer 124.

More specifically, the simplified-block diagram of FIG. 8 is of a prior art mask inspection system 110, that includes a stage 112 for carrying a substrate 114 to be inspected, an optical subsystem 116, a data base adaptor 218, an electronics subsystem 120, a display 122, a control computer 124, and a keyboard 126. The stage 112 is a precision device driver under control of subsystem 120 and capable of moving the substrate 114 under the test relative to the optical axes of optical subsystem 116 so that all or any selected part of the substrate surface may be inspected. Optical subsystem 116 includes a light source 130 and related optics which cause a beam of light to be deflected back and forth over a small angle as viewed by the substrate 114. The light beam emitted by light 130 is deflected by the combination of two acousto-optic elements; an acousto-optic prescanner 140 and an acousto-optic scanner 142. When the light beam emerges from the scanner 142 it then enters a cube beam splitter 160. The beam next passes through an objective lens 182 which focuses the beam onto the substrate 114. Light passing through the substrate 114 is then collected by a condenser lens 184 and focused onto the transmission detector 134.

With a gray scale value assigned to each pixel in the defect area, the probable center of the defect is selected (16) and the coordinates of the pixel at that location are noted. Next the polarity (white or black) of the defect is determined (18) by comparing the gray scale value of the pixel at the selected probable center of the defect to the gray scale value of at least one reference pixel a number of pixels spaced apart from the probable center pixel (e.g., 10 pixels to the right). If the gray scale value of the selected probable center pixel is less than the gray scale value of the reference pixel the defect is considered to be black, or have negative energy. If the gray scale value of the selected probable center pixel is greater than the gray scale value of the reference pixel, the defect is considered to be white, or have positive energy.

Alternatively, reference pixels 2, 5, 7 and 10 pixel positions away from the probable center pixel could each be checked and if gray scale value successively from reference pixel to reference pixel continues to drop then the defect is considered to be white, or have positive energy. Whereas, if the gray scale values successively from reference pixel to reference pixel continues to rise then the defect is considered to be black, or have negative energy. However, if the gray scale value of the reference pixels at first moves in one direction and then changes direction the further that reference pixel is from the probable center pixel, the probable center pixel is near a line edge and the reference pixel progression will have to be performed in another direction without encountering a line edge.

Figure 2:
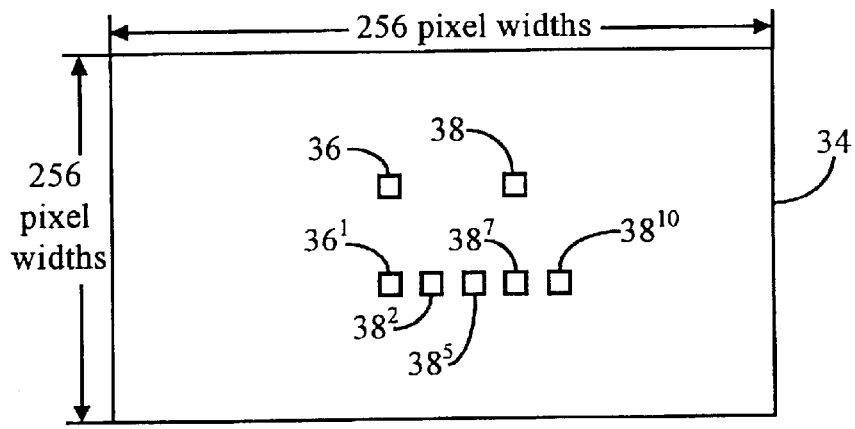
FIG. 2 illustrates a 256 by 256 pixel grid image that is used by the present invention as a general work area for the present invention, and here illustrates the determination of the polarity of a defect.

FIG. 2 illustrates a pixel grid image 34 as discussed above with respect to blocks 12 and 14 above. Additionally, there is shown a probable center pixel 36 of that image and a single reference pixel 38 that is used as discussed above with respect to blocks 16 and 18 to determine the polarity of the defect. Alternatively, FIG. 2 also shows a probable center pixel 36' and reference pixels $38^2$, $38^5$, $38^7$ and $38^{10}$, as discussed in the alternative approach that avoids making the decision when there is a line edge in close proximity to the probable center pixel.

This procedure to identify the defect as either black or white could be refined further by considering a second reference pixel either further away from the selected probable center pixel, or in another direction than the first reference pixel, if the gray scale differences between the first considered reference pixel and the selected probable center pixel are closer together than a preselected difference. Still other distances and directions could be tried until a more definitive value difference value is observed to better determine the polarity of the defect.

Referring again to FIG. 1, with the polarity of the defect determined, a coarse center of the defect (20) is determined by finding the pixel in the defect with the minimum or maximum (according to the polarity) gray scale value. This is accomplished by comparing the gray scale values of the pixels in a square pixel window around the selected coarse center pixel (e.g., 3 by 3 pixels with the selected coarse center pixel in the center). If the gray scale value of one of those pixels in comparison with the selected pixel is determined to be higher (white polarity defect), or lower (black polarity defect), that pixel is selected as the new coarse center pixel and a second pixel window of the same size, centered about the new coarse center pixel, is observed and the search is performed again. This process can be repeated as many times as necessary to find a better choice of the coarse center pixel of the defect. To insure accuracy this test can be repeated at least some minimum number of times, perhaps 5, to fully search for and identify the best coarse center pixel.

Figure 3:
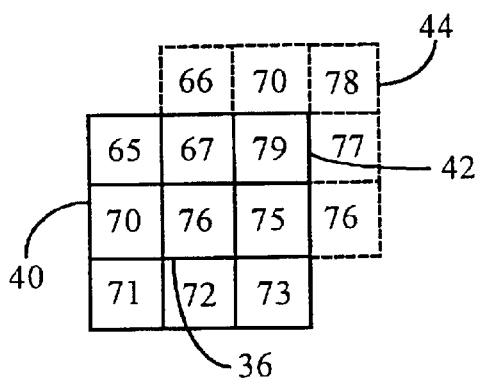
FIG. 3 illustrate a 3 by 3 pixel window that is used to determine the coarse center pixel.

FIG. 3 illustrates the use of a square pixel window 40 of the type described above with respect to block of FIG. 1. Here, for the first step at the determination of the coarse center pixel with the probable center pixel 36 first selected as the coarse center pixel with the first square 3 by 3 pixel window 40 drawn around it. In each of the squares of window 40 a representative gray scale value has been shown with 76 having been assigned to pixel 36. Then, the gray, scale value of each of the surrounding pixels is compared to the value of pixel 36 to determine if there is a pixel that has a gray scale value that is higher than that of pixel 36. In this example it can be seen that pixel 42 has a gray scale value that is 79 versus the 76 of pixel 36, thus pixel 42 is selected as the next coarse center pixel. Again a 3 by 3 pixel window 44 is drawn around pixel 42 and the surrounding gray scale values of those pixels are compared to the gray scale value of pixel 42 in search of another pixel with a higher gray scale value. In this example, pixel 42 has the highest gray scale value and therefore would be selected as the coarse center pixel of the defect.

Returning again to FIG. 1, with the coarse center pixel of the defect determined, the sub pixel center of the defect can be more finely determined (22) by using a sub pixel interpolation routine. Using the gray scale values for the best coarse center pixel, and surrounding pixels (e.g., the pixel on either side of the coarse center pixel in each direction of interest—x, y and diagonals perhaps), a fine approximation of the defect center, to within less than a pixel dimension (e.g., to within 0.1 pixels) can be determined.

Figure 4:
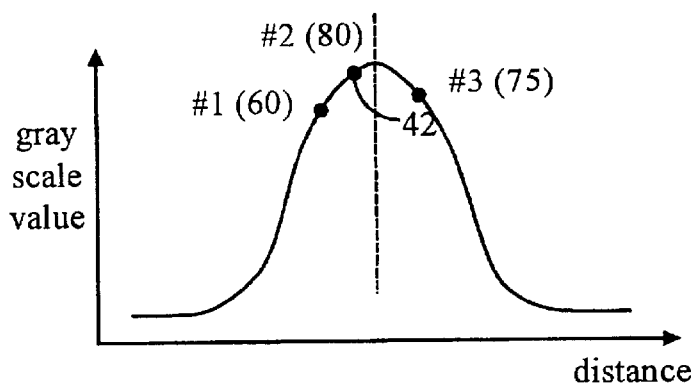
FIG. 4 illustrates a sub pixel peak gray scale value location routine to perform a fine location of the center of a defect.

FIG. 4 shows an example of a sub pixel interpolation routine in one direction. Here, the gray scale level variation versus distance for a representative defect is shown with the location and gray scale values of the coarse center pixel 42 (here numbered 2) and the nearest pixels on opposite sides thereof along the same axis (here numbered 1 and 3, respectively). Also, for purposes of this illustration, pixels 1, 2 and 3 each has a gray scale value of 60, 80 and 75, respectively. Also from the defect gray scale curve it can be seen that coarse center pixel 42 is not quite at the peak gray scale value of the defect along the representative axis. The fine center of the defect can be located with the following formula: ##EQU1## where $x_1$ is the gray scale value of pixel 1;

$x_2$ is the gray scale value of pixel 2; and X $x_3$ is the gray scale value of pixel 3.

Using the sample gray scale values of FIG. 4a, equation (1) yields: ##EQU2## thus the fine center pixel location is 0.0697 of a pixel width closer to pixel 3 from pixel 2, or 6.97% of a pixel width from the center of pixel 2 in the direction of pixel 3.

Again returning to FIG. 1, with the center of the defect determined, the size of the defect, or physical extent of the defect in several directions (24), can next be determined. This is accomplished by first noting the gray scale value of the pixel at the center of the defect. That gray scale value is then compared to the gray scale value of the next adjacent pixel in a selected direction. If the difference in gray scale values is greater than a preselected level (e.g., 2), the pixel location is incremented in the same direction by one with the gray scale value of that next pixel compared to the previous adjacent pixel. If that difference value is still greater than the same preselected level, that process continues in that same direction until the difference value does not exceed the preselected level. Once the pixel where the difference value does not exceed the preselected value is determined, that pixel is considered to be the extent of the defect, or on the edge of the defect, in that direction. The same procedure is performed in other selected directions to similarly find the extent, or edge of the defect, in each of those directions. This effectively defines the edge of the defect, or, since the pixels are square, substantially a box around the defect. How many directions in which the comparisons are performed is optional and may be partly dependent on prior knowledge as to the approximate location of the defect relative to other features on the reticle (e.g., proximity to a region of the opposite polarity such as a trace and an opaque region, corner of an opaque or transparent region) of the accuracy to which the extent of the defect is to be determined (e.g., it may be desirable to perform the same function diagonally outward from the center of the defect, or perhaps radially every 10.degree.).

FIG. 5 illustrates, as a bell shaped curve 48, how the gray scale values of the individual pixels of a defect might vary with distance from the gray scale value of the pixel at the fine center, F, of the defect along one axis. Thus, to determine the extent of the defect the gray scale value of adjacent pixels are compared with each other until the difference in gray scale values between two adjacent pixel along the same axis from the center pixel, F, is below a preselected threshold value. Using the values shown in FIG. 5 and assuming that the threshold value is 2, the pixel at location 50 will represent the extent of the defect to the left of the defect center since there is only a difference of 1 with the gray scale value of the next pixel to the right, whereas the differences between all other pixels between pixel 50 and the center pixel are all greater than 2. As stated above, this technique is used in as many other directions as desired to find the extent of the defect in the pixel grid image 34.

Back to FIG. 1, with the extent of the defect determined it is now possible to determine the transmittible energy level of the defect (26). First, the pixel energy of the defect is determined by summing all gray scale values of all of the pixels that are encompassed by the extent of the defect in each direction considered above. Second, in order to measure the energy difference provided by the defect alone, it is necessary to subtract an approximation of the background energy value that would have been present had there not been a defect, or in other words the background noise of this region of the reticle image. A variation in the transmittable energy level of a defect could result from areas that are totally transparent, to those that are somewhat translucent, to those that are totally opaque. The causation for those types of variations in transmittible energy level are numerous. Perhaps the chrome layer on the reticle is thinner in some locations, perhaps there is a scratch that extends substantially through, or all the way through, the chrome layer, perhaps there is a chemical stain on the transparent or opaque regions on the reticle that may or may not impede the transmission of light through the transparent regions . . . the list is virtually endless.

One way to approximate the background energy of the defect is to sum together the gray scale values for all of the pixels in an immediately adjacent region to the pixel grid image (see 12 above) that is the same size and shape as the determined extent of the defect. For best results, this immediately adjacent region should be defect free, and of the same polarity as the defect. The summed energy from that adjacent region is then considered to be approximately what would have been the background energy level of the defect region and is therefore subtracted from the summed energy level of the defect region to get a more accurate measure of the transmittible energy level of the defect region.

To obtain a more accurate approximation of the background energy of the defect region, multiple adjacent regions of the same size and shape can be used with the energy levels of those regions averaged together. Then that averaged energy value would be subtracted from the energy value of the defect region. Through the use of the average level, the effects of some anomalies or system noise in the regions being used to determine the background energy level would be reduced.

FIG. 6 illustrates the pixel grid image 34 for the defect of interest with the extent of that defect shown by outline 52. First the total of the gray scale values for all pixels within that defined defect extent are summed together. Then an area of the same size and shape 54 is considered adjacent to the extent of the defined defect with the gray scale values of all of the pixels within that area added together to determine an approximation of the background gray scale energy value for the defined defect area 52. The value for area 54 is then subtracted from the value of defect area 52 to determine the actual level of transmittible energy level of defect area 52. Alternatively, as discussed above, multiple adjacent areas 54, 56 and 58, of the same size and shape can also be defined adjacent to defect area 52 with the total gray scale energy level for all of the pixels within those areas added together and the total then divided by 3 in this example to determine an average background energy level to be subtracted from the energy level of defect area 52.

Referring to FIG. 1, it is also known that the proximity of a defect in a reticle to an edge in the pattern on the reticle can have an amplified effect on the printing of the defect to the substrate. It is necessary to then determine that proximity, if it exists. The proximity of a defect to a pattern edge on a reticle (28) is then determined by searching in numerous directions outside the determined extent of the defect for a gradient (geometry edge) where the gray scale value rapidly approaches the opposite polarity of the defect region. Linear sub pixel interpolation is then used to determine the 50% point of the gradient (i.e., where the gray scale value is one half the difference in the maximum gray scale levels on each side of that pixel located at the point of transition). With the transition pixel location determined, the distance between the transition pixel and the center pixel of the defect in microns is the distance to the reticle edge from the defect.

FIG. 7a illustrates the typical gray scale values of pixels that form the edge of a line on a reticle. In this example pixels $P.sub.1$, $P.sub.2$, $P.sub.3$ and $P.sub.4$ are shown, respectively, as having a relative gray scale value of a few percent, 30%, 68% and 100%. Further, as stated above, the location of the edge of a line is defined as where the relative gray scale value is 50%. Since there is no pixel that has the 50% value, linear sub pixel interpolation is used to determine a close approximation to that location. In this example it can be seen that location is somewhere between the centers of pixels $P.sub.2$ and $P.sub.3$. In FIG. 7b the portion of the curve that includes the relative values and spacing of pixels $P.sub.2$ and $P.sub.3$ are shown with a straight line drawn between those two points on the curve. Thus, since the relative values for those points are 68% and 30%, a difference of 38, and the difference of 50% from 68% is 18, the location of the 50% point will be 18/38 (9/19) of a pixel width from the center of pixel $P.sub.3$ to the center of pixel $P.sub.2$. Thus, the distance from the line edge to the defect center pixel, F, is the distance from the defect center pixel, F, to the center of pixel $P.sub.2$ plus 9/18 of a pixel width.

As stated above, (see FIG. 1) other factors contribute (30) to whether a defect on a reticle prints onto a substrate (e.g., type of resist, type of stepper, illumination frequency, etc.) with different weighting factors being assignable for each of those variables once it is known what chemicals and equipment a manufacturer uses. Thus, isolated defect printability is predicted by applying selected weighting to the energy of the defect where those weighting factors are attributable to a particular wafer fab process. Similarly, near edge defect printability is also determined by both that distance and the particular wafer fab process that is used. Thus, other weighting factors must be applied to the energy level of the defect to predict printability of those defects that are near an edge. There are therefore two factors that work together to determine the near edge weighting factor to use: how close a defect is to an edge with a higher weighting value necessary the closer the defect is to the edge; and the particular wafer fab process being used.

It should be noted that the above discussion has been for a single defect, and it should further be understood that for multiple defects that may be found in a reticle the above described procedure would be repeated for each such defect that was not otherwise incorporated into the defect extent of an earlier processed defect.

It should further be noted that the above discussion has included a group of procedures, with some of those procedures being optimization procedures, and that if some of those procedures are not performed, improvement over the prior art will still be achieved. For example, those procedures corresponding to blocks 20, 22, 28 and 32 are secondary procedures that can be omitted with a useful result still being achieved.

While the present invention has been described having several optional steps, it is contemplated that persons skilled in the art, upon reading the preceding descriptions and studying the drawings, will realize various alternative approaches to the implementation of the present invention, including several other optional steps, or consolidations of steps. It is therefore intended that the following appended claims be interpreted as including all such alterations and modifications that fall within the true spirit and scope of the present invention.

What is claimed is:

1. A computer program stored on a computer readable medium for determining the presence of a defect on a reticle or photomask, said computer program comprising:

instructions for creating a pixel grid image of a first portion of said reticle or photomask, said pixel grid image having a plurality of associated individual pixel images of said reticle or photomask;

instructions for determining a coarse center pixel of said pixel grid image;

instructions for determining a region of physical extent of said pixel grid image;

instructions for assigning a gray scale value to each of said associated individual pixel images of said pixel grid image;

instructions for summing together said gray scale values of all of said pixels included within said pixel grid image to determine a first summed energy level of said pixel grid image;

instructions for selecting a similar region adjacent to said pixel grid image wherein said adjacent region is defect free;

instructions for summing together gray scale values of all pixels included within said adjacent region to determine a second summed energy level;

instructions for subtracting said second summed energy level from said first summed energy level; and instructions for determining if said pixel grid image contains a defect.

2. A computer program as recited in claim 1 further comprising:

instruction for determining a transmissivity energy level of said pixel grid image.

3. A computer program as recited in claim 2 further comprising:

instructions for determining printability of said defect which is located within said pixel grid image by applying a weighting factor to said transmissivity energy level, said weighting factor being a combination of several variables contributed by a particular wafer fabrication process being used to produce a substrate using said reticle or photomask.

4. A computer program as recited in claim 1 wherein said adjacent region has the same size and shape as said first portion of said reticle or photomask.

5. A computer program stored on a computer readable medium for determining the presence of a defect on a reticle or photomask, said computer program comprising:

instructions for creating a pixel grid image of a first portion of said reticle or photomask, said pixel grid image having a plurality of associated individual pixel images of said reticle or photomask;

instructions for determining a coarse center pixel of said pixel grid image;

instructions for determining a region of physical extent of said pixel grid image;

instructions for assigning an energy value to each of said associated individual pixel images of said pixel grid image;

instructions for summing together said energy values of all of said pixels included within said pixel grid image to determine a first summed energy level of said pixel grid image;

instructions for selecting a reference region which is similar to said pixel grid image in size and shape wherein said reference region is defect free;

instructions for summing together energy values of all pixels included within said reference region to determine a second summed energy level;

instructions for comparing said second summed energy level against said first summed energy level; and instructions for determining if said pixel grid image contains a defect.

6. A computer program as recited in claim 5 further comprising:

instruction for determining a transmissivity energy level of said pixel grid image.

7. A computer program stored on a computer readable medium for determining the presence of a defect on a reticle or photomask, said computer program comprising:

instructions for creating an image of a first portion of said reticle or photomask, said image being made up of a plurality of individual sub-regions;

instruction for determining a coarse center of said image;

instruction for determining a region of physical extent of said image;

instructions for assigning an energy value to each of said sub-regions;

instructions for summing together said energy values of all of said sub-regions to determine a first summed energy level;

instructions for comparing a second summed energy level against said first summed energy level wherein said second summed energy level corresponds to a summation of energy values of all sub-regions within a reference image stored in a reference database; and instructions for determining if said image contains a defect.

8. A computer program as recited in claim 7 further comprising:

instruction for determining a transmissivity energy level of said image.

* * * * *